United States Patent
Tal et al.

(10) Patent No.: US 12,073,018 B2
(45) Date of Patent: Aug. 27, 2024

(54) MULTIPLE GAZE DEPENDENT ILLUMINATION SOURCES FOR RETINAL EYE TRACKING

(71) Applicant: APPLE INC., Cupertino, CA (US)

(72) Inventors: Eran Tal, Petach Tivka (IL); Ariel Lipson, Tel Aviv (IL)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 18/026,881

(22) PCT Filed: Sep. 10, 2021

(86) PCT No.: PCT/US2021/049783
§ 371 (c)(1),
(2) Date: Mar. 17, 2023

(87) PCT Pub. No.: WO2022/066431
PCT Pub. Date: Mar. 31, 2022

(65) Prior Publication Data
US 2023/0333640 A1  Oct. 19, 2023

Related U.S. Application Data

(60) Provisional application No. 63/081,545, filed on Sep. 22, 2020.

(51) Int. Cl.
*G06F 3/01* (2006.01)
*G02B 27/01* (2006.01)
*G06F 21/32* (2013.01)

(52) U.S. Cl.
CPC .............. *G06F 3/013* (2013.01); *G02B 27/01* (2013.01); *G02B 27/017* (2013.01); *G06F 3/012* (2013.01);
(Continued)

(58) Field of Classification Search
CPC .......... G06F 3/012; G06F 3/013; G06F 21/32; G02B 27/01; G02B 27/017; G06T 2207/30041
(Continued)

(56) References Cited

U.S. PATENT DOCUMENTS

| 5,325,133 A * | 6/1994 | Adachi | G06V 40/193 |
| | | | 345/157 |
| 8,025,405 B2 * | 9/2011 | Rehnstrom | A61B 3/0008 |
| | | | 351/210 |

(Continued)

FOREIGN PATENT DOCUMENTS

| WO | 2015/081313 A2 | 6/2015 |
| WO | 2019/036196 A1 | 2/2019 |

OTHER PUBLICATIONS

(PCT) European Patent Office (ISA/EP), International Search Report and Written Opinion of the International Searching Authority, International Application No. PCT/US2021/049783, 20 pages, Jan. 3, 2022.

*Primary Examiner* — Tom V Sheng
(74) *Attorney, Agent, or Firm* — Thompson Hine LLP (57) ABSTRACT

Various implementations disclosed herein include devices, systems, and methods that provide retinal imaging-based gaze tracking In some implementations, a user's gaze is tracked based on a retinal imaging technique that selectively uses a subset of multiple light sources (222, 310, 610) that illuminate different portions of the user's retina (352). In some implementations, a method (700) includes selecting (710) a subset of light sources, where the subset of the light sources includes less than all of the light sources. In some implementations, one or more portions of a retina (352) are illuminated (720) by producing light using the subset of the light sources. In some implementations, sensor data is received (730) at a sensor (224, 340, 814), the sensor data corresponding to the light detected during retinal imaging, and an eye characteristic is determined (740) based on the sensor data.

19 Claims, 8 Drawing Sheets

(52) U.S. Cl.
CPC .... *G06F 21/32* (2013.01); *G06T 2207/30041* (2013.01)

(58) Field of Classification Search
USPC .......................................................... 345/156
See application file for complete search history.

(56) References Cited

U.S. PATENT DOCUMENTS

| | | |
|---|---|---|
| 8,824,779 B1 | 9/2014 | Smyth |
| 10,656,707 B1 * | 5/2020 | Sharma ................... G06F 3/041 |
| 11,153,512 B1 * | 10/2021 | Sharma .............. G02B 27/0172 |
| 11,474,358 B2 * | 10/2022 | Meitav ...................... G06T 7/73 |
| 2006/0238707 A1 * | 10/2006 | Elvesjo ................. A61B 3/113 |
| | | 351/209 |
| 2015/0189266 A1 * | 7/2015 | Zhou .................... H04N 13/271 |
| | | 348/54 |
| 2015/0199006 A1 * | 7/2015 | He .......................... G06F 3/013 |
| | | 345/158 |
| 2015/0241967 A1 * | 8/2015 | Saripalle ................ G06F 3/013 |
| | | 382/195 |
| 2016/0081547 A1 | 3/2016 | Gramatikov et al. |
| 2016/0314729 A1 * | 10/2016 | Gutierrez ............... G09G 3/001 |
| 2018/0350070 A1 * | 12/2018 | Ishii .......................... G06T 7/70 |
| 2020/0089316 A1 * | 3/2020 | Raskar ................... G06F 3/013 |
| 2020/0372678 A1 * | 11/2020 | Farmer ................... G06F 3/013 |

\* cited by examiner

MULTIPLE GAZE DEPENDENT ILLUMINATION SOURCES FOR RETINAL EYE TRACKING

CROSS-REFERENCE TO RELATED APPLICATIONS

This patent application is the national stage of International Application No. PCT/US2021/049783 filed on Sep. 10, 2021, which claims the benefit of U.S. Provisional Patent Application No. 63/081,545 filed on Sep. 22, 2020, entitled "MULTIPLE GAZE DEPENDENT ILLUMINATION SOURCES FOR RETINAL EYE TRACKING," each of which is incorporated herein by this reference in its entirety.

TECHNICAL FIELD

The present disclosure generally relates to providing retinal imaging-based eye tracking of a user of an electronic device and, in particular, to systems, methods, and devices that provide retinal imaging-based eye tracking of a user of an electronic device using multiple illumination sources.

BACKGROUND

Retinal imaging-based tracking systems generally have both an illumination source to direct light towards the retina and an image sensor to generate images including light reflected from the retina. Drawbacks of such tracking systems include the relatively significant amount of power used by the illumination sources and unwanted reflections (glare) from eye surfaces other than the retina, e.g., cornea, crystalline lens, etc.

SUMMARY

Various implementations disclosed herein include devices, systems, and methods that provide retinal imaging-based gaze tracking. In some implementations, a user's gaze is tracked based on a retinal imaging technique that selectively illuminates a subset of multiple light sources to direct light towards one or more portions of the user's retina. In some implementations, the subset of the light sources is used in retinal imaging to provide better gaze tracking by reducing glare, reducing image saturation, reducing imaging computation, or reducing energy consumption.

In some implementations, retinal imaging-based gaze tracking uses a subset of the light sources that are each configured to direct light to a different location (e.g., region) on the retina. Based on a map of the retina, a selected subset of light sources may be used during static eye gaze conditions (e.g., about 80% of the time). When the eye makes a big movement, all or most of the light sources of the multiple light sources may be enabled to concurrently evaluate the whole retina (e.g., entire retinal field) to identify a new gaze direction or gaze landing point. When the new gaze direction is determined, the subset of light sources may again be used. In some implementations, the subset of light sources of the multiple light sources is different for each of a plurality of different gaze directions. In some implementations, the multiple light sources may use a single collimation lens or a collimating lens for every individual light source. In some implementations, the multiple light sources is an array of light sources (e.g., 2D/3D array).

In some implementations, unwanted glare (reflection) from other surfaces of the eye including the cornea and crystalline lens caused by specific ones of the multiple light sources may be identified (e.g., during enrollment) and reduced by disabling those specific light sources. In some implementations, energy consumption may be reduced by disabling specific light sources during retinal imaging-based gaze tracking.

In some implementations, a method includes selecting a subset of the light sources, the subset of the light sources including less than all of the light sources. In some implementations, one or more of the subset of the light sources is illuminated to direct light towards one or more portions of the user's retina. Then, sensor data is received at a sensor, where the sensor data corresponds to the light detected using retinal imaging, and an eye characteristic is determinized based on the sensor data.

BRIEF DESCRIPTION OF THE DRAWINGS

So that the present disclosure can be understood by those of ordinary skill in the art, a more detailed description may be had by reference to aspects of some illustrative implementations, some of which are shown in the accompanying drawings.

In accordance with common practice, the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DESCRIPTION

Numerous details are described in order to provide a thorough understanding of the example implementations shown in the drawings. However, the drawings merely show some example aspects of the present disclosure and are therefore not to be considered limiting. Those of ordinary skill in the art will appreciate that other effective aspects or variants do not include all of the specific details described herein. Moreover, well-known systems, methods, components, devices and circuits have not been described in exhaustive detail so as not to obscure more pertinent aspects of the example implementations described herein.

Figure 1:
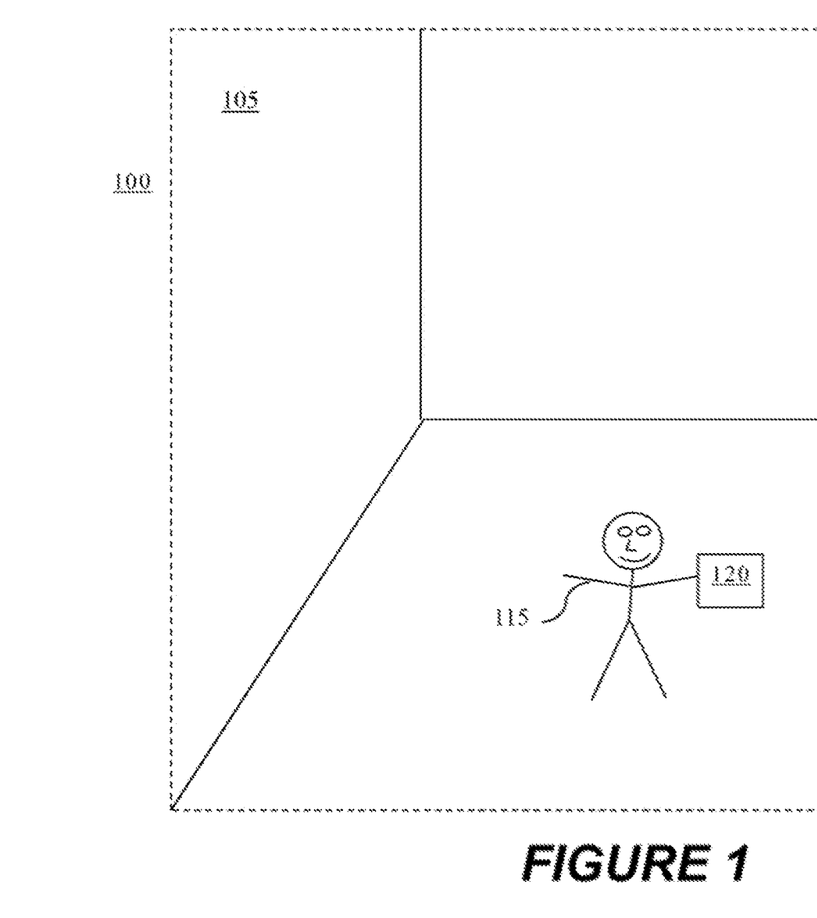
FIG. 1 illustrates an example operating environment in accordance with some implementations.

FIG. 1 illustrates an example operating environment 100 in which electronic device 120 is used in physical environment 105. A physical environment refers to a physical world that people can interact with and/or sense without the aid of electronic systems. Physical environments, such as a physical park, include physical articles, such as physical trees, physical buildings, and physical people. People can directly sense and/or interact with the physical environment, such as through sight, touch, hearing, taste, and smell.

In the example of FIG. 1, the device 120 is illustrated as a single device. Some implementations of the device 120 are hand-held. For example, the device 120 may be a mobile phone, a tablet, a laptop, and so forth. In some implementations, the device 120 is worn by a user. For example, the device 120 may be a watch, a head-mounted device (HMD), and so forth. In some implementations, functions of the device 120 are accomplished via two or more devices, for example additionally including an optional base station. Other examples include a laptop, desktop, server, or other such device that includes additional capabilities in terms of power, CPU capabilities, GPU capabilities, storage capabilities, memory capabilities, and the like. The multiple devices that may be used to accomplish the functions of the device 120 may communicate with one another via wired or wireless communications.

Various implementations disclosed herein include devices, systems, and methods that implement retinal imaging-based gaze tracking. In some implementations, illumination for retinal imaging-based gaze tracking is separated into an array of illuminators, which each illuminate a different region on the retina. In some implementations, by turning on a specific illuminator or a subset of the illuminators of the array of illuminators, power consumption or glare is reduced during gaze tracking. In some implementations, a specific illuminator or a subset of the illuminators of the array of illuminators is chosen based on a gaze direction of the user. The subset of the illuminators is less than all of the array of illuminators. For example, when the eye gaze is static, reduced illumination or more selective illumination may be used. In some implementations, the array of illuminators includes multiple addressable light sources such as vertical-cavity surface-emitting lasers (VCSEL) on Silicon, or light emitting diodes (LEDs).

Figure 2:
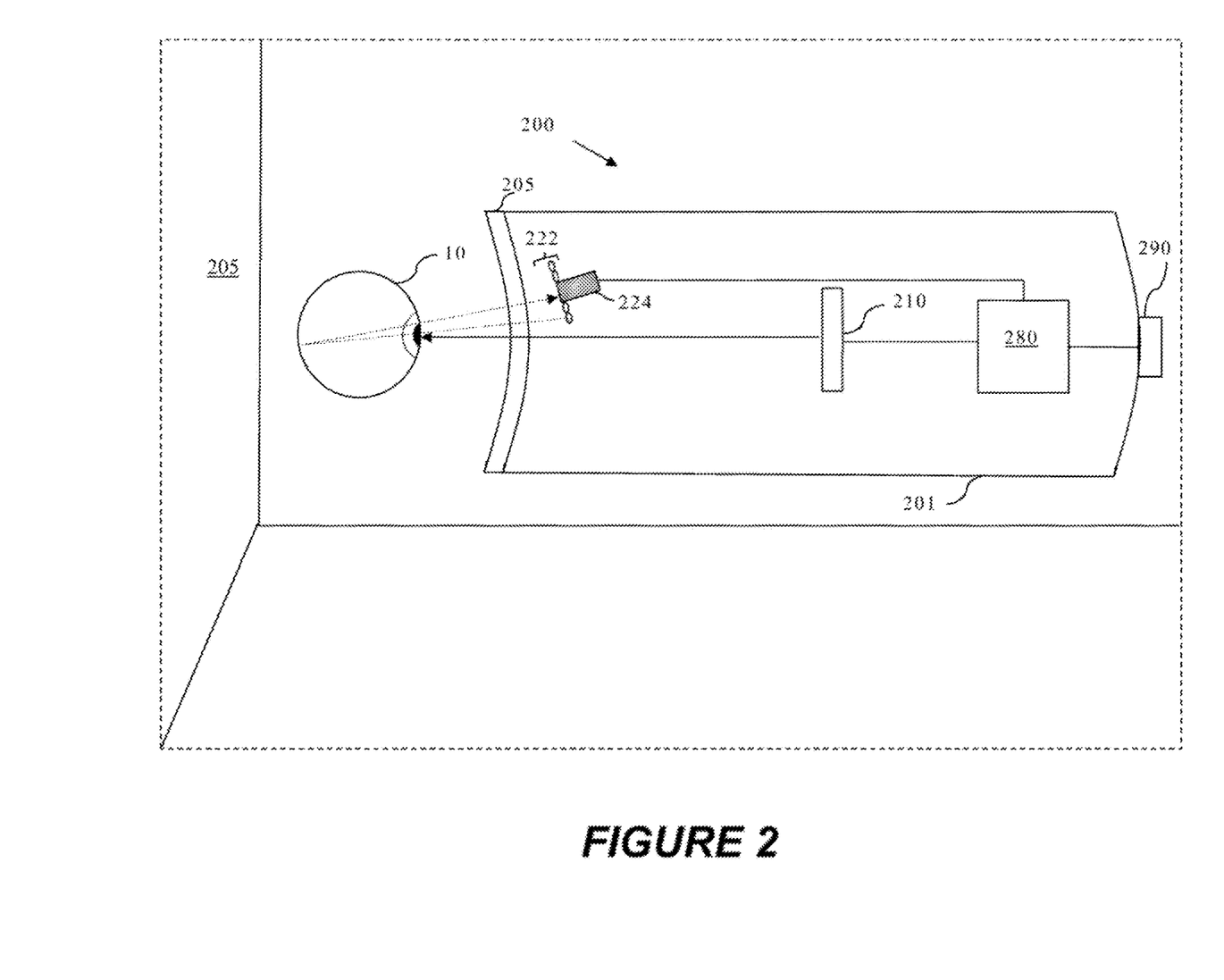
FIG. 2 illustrates an exemplary head mounted device (HMD) in accordance with some implementations.

FIG. 2 illustrates a block diagram of a HMD 200 in accordance with some implementations. The head-mounted device 200 includes a housing 201 (or enclosure) that houses various components of the head-mounted device 200. The housing 201 includes (or is coupled to) an eye pad 205 disposed at a proximal (to the user 10) end of the housing 201. In various implementations, the eye pad 205 is a plastic or rubber piece that comfortably and snugly keeps the head-mounted device 200 in the proper position on the face of the user 10 (e.g., surrounding the eye of the user 10).

The housing 201 houses a display 210 that displays an image, emitting light towards onto the eye of a user 10. In various implementations, the display 210 emits the light through an eyepiece (not shown) that refracts the light emitted by the display 210, making the display appear to the user 10 to be at a virtual distance farther than the actual distance from the eye to the display 210. For the user to be able to focus on the display 210, in various implementations, the virtual distance is at least greater than a minimum focal distance of the eye (e.g., 7 cm). Further, in order to provide a better user experience, in various implementations, the virtual distance is greater than 1 meter.

Although FIG. 2 illustrates a head-mounted device 200 including a display 210 and an eye pad 205, in various implementations, the head-mounted device 200 does not include a display 210 or includes an optical see-through display without including an eye pad 205.

The housing 201 also houses a pupil assessment system including one or more light sources 222, image sensor 224, and a controller 280. The one or more light sources 222 emit light towards the eye of the user 10 that reflects light (e.g., a directional beam) that can be detected by the sensor 224. Based on the reflections, the controller 280 can determine pupil characteristics of the user 10. As another example, the controller 280 can determine a pupil center, a pupil size, gaze direction, or a point of regard. Thus, in various implementations, the light is emitted by the one or more light sources 222, reflects off the eye of the user 10, and is detected by the sensor 224. In various implementations, the light from the eye of the user 10 is reflected off a hot mirror or passed through an eyepiece before reaching the sensor 224.

The display 210 may emit light in a first wavelength range and the one or more light sources 222 may emit light in a second wavelength range. Similarly, the sensor 224 may detects light in the second wavelength range. In various implementations, the first wavelength range is a visible wavelength range (e.g., a wavelength range within the visible spectrum of approximately 400-700 nm) and the second wavelength range is a near-infrared wavelength range (e.g., a wavelength range within the near-infrared spectrum of approximately 700-1400 nm).

In some implementations, one or more of the light sources 222 each point to a different region on the retina. In some implementations, retinal imaging-based gaze tracking uses a subset of the light sources 222. Based on a map of the retina obtained during enrollment, the subset of the light sources 222 used for retinal imaging-based gaze tracking may be used during static eye gaze conditions (e.g., about 80% of the time). When the eye makes a big movement, all or more than the subset of the light sources 222 may be enabled to concurrently evaluate the whole retina (e.g., entire retinal field) to identify a new gaze direction or gaze landing point. When the new gaze direction is determined, the subset that is less than all of the light sources 222 may again be used. In some implementations, the subset of light sources 222 is different for each of a plurality of different gaze directions.

In some implementations, the one or more other light sources (not shown) emit light towards the eye of the user which reflects in the form of one or more glints off the surface of the eye.

In various implementations, the sensor 224 is a frame/shutter-based camera that, at a particular point in time or multiple points in time at a frame rate, generates an image of the eye of the user 10. Each image includes a matrix of pixel values corresponding to pixels of the image which correspond to locations of a matrix of light sensors of the camera.

In various implementations, the camera 224 is an event camera comprising a plurality of light sensors (e.g., a matrix of light sensors) at a plurality of respective locations that, in response to a particular light sensor detecting a change in intensity of light, generates an event message indicating a particular location of the particular light sensor.

In various implementations, pupil characteristic assessment is used to facilitate gaze tracking, which may be used to enable user interaction (e.g., the user 10 selects an option on the display 210 by looking at it), provide foveated rendering (e.g., present a higher resolution in an area of the display 210 the user 10 is looking at and a lower resolution elsewhere on the display 210), or reduce geometric distortion (e.g., in 3D rendering of objects on the display 210).

Figure 3:
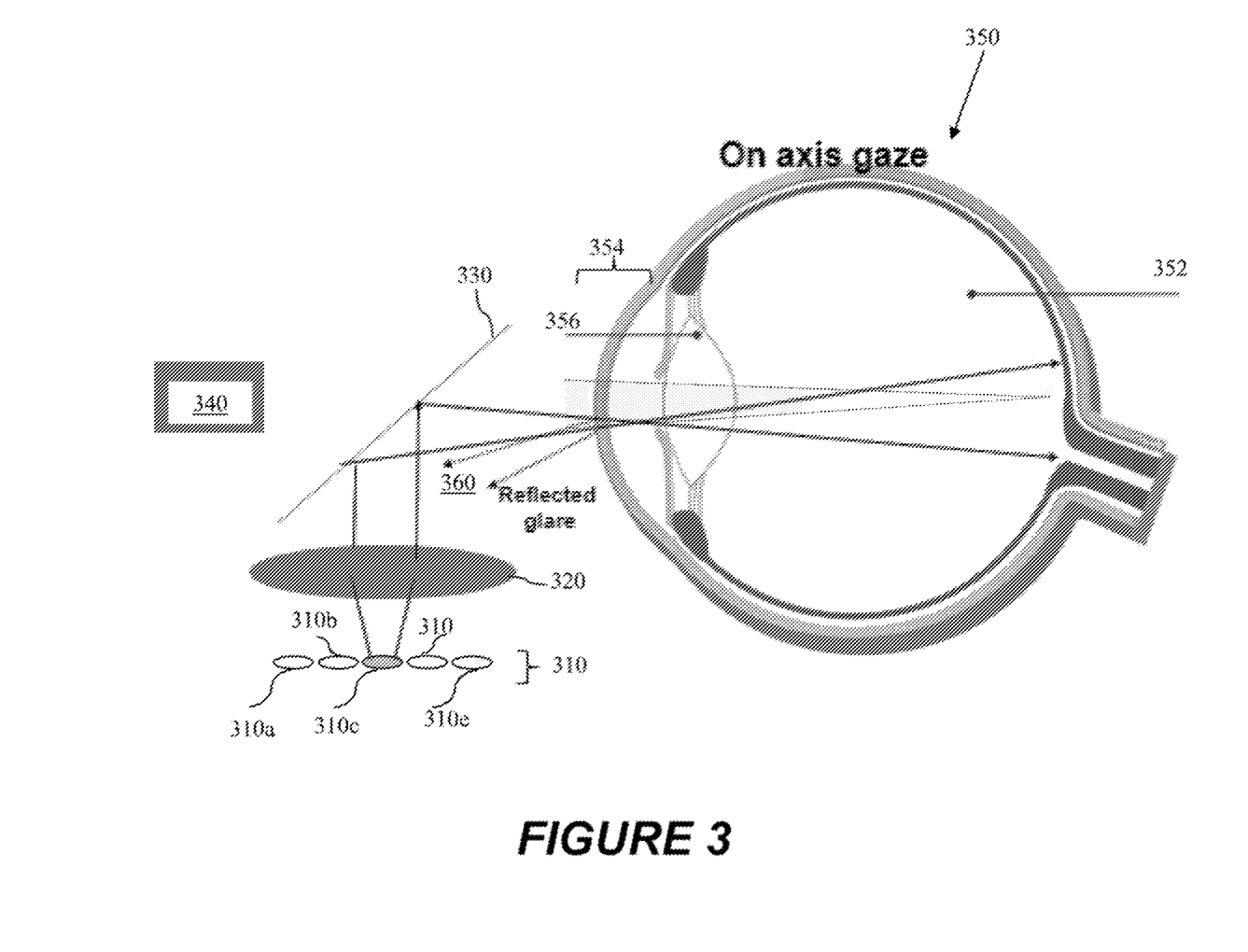
FIG. 3 is a block diagram that illustrates an exemplary tracking system that selectively uses a subset of multiple light sources to illuminate one or more portions of a retina for gaze tracking in accordance with some implementations.

FIG. 3 is a block diagram that illustrates an exemplary eye tracking system that selectively uses a subset of multiple light sources to illuminate one or more portions of a retina for gaze tracking in accordance with some implementations. In some implementations, using a subset of the multiple light sources in retinal imaging provides better gaze tracking by reducing glare, reducing image saturation, reducing imaging computation, or reducing energy consumption.

As shown in FIG. 3, multiple lights sources 310, a collimator 320, a beam splitter 330 and an image sensor 340 form a retinal imaging-based gaze tracking system. In some implementations, the multiple light sources 310 include multiple addressable light sources 310a, 310b, ..., 310e that when enabled each illuminate different portions of a retina 352 of an eye 350.

As shown in FIG. 3, the multiple lights sources 310 produce light that is reflected off the beam splitter 330 at an angle to provide light that illuminates different portions of the retina 352. The reflected light from the retina 352 passes through the beam splitter 330 and is captured by the image sensor 340 (e.g., IR camera). As shown in FIG. 3, the only enabled light source 310c of the light sources 310 uses the beam splitter 330 to provide approximately on-axis illumination. The same effect of rendering a virtual location of a light source to be substantially coaxial with the camera axis can be achieved using different types of waveguides, including using mirrors, fiber optics, diffractive optical elements, holographic elements, etc.

In some implementations, the subset of the multiple light sources 310 are selectively turned on depending upon gaze direction. In some implementations, selectively enabling a subset of the multiple light sources 310 is related to the portion of the retina 350 that is viewable by the image sensor 340 in a current image, which is related to the gaze direction (e.g., eye orientation). In some implementations, the subset of the multiple light sources 310 chosen for each different gaze direction is different.

Generally, the gaze direction of the eye 350 is stable or static 80% of the time. In some implementations, the static gaze direction of the eye 350 allows for more selective illumination (e.g., less illumination or less energy) using the subset of the multiple light sources 310. In some implementations, the subset of the multiple light sources 310 may be intermittently disabled or pulsed to further reduce energy consumption. Alternatively, an illumination strength of the subset of the multiple light sources 310 may be reduced to further reduce energy consumption. In some implementations, the static gaze direction includes minor movements of the eye such as micro-saccades or the like. In some implementations, the static gaze direction includes minor movements of the eye that are less than a movement threshold. In some implementations, when the gaze direction of the eye 350 is static, as few as a single light source of the multiple light sources 310 may be used to monitor or track the gaze direction of the eye 350. For example, two or more light sources 310 that actually direct light towards the retina 352 in a field of view (FOV) of the image sensor 340 for a gaze direction are selected as the subset of light sources 310. In some implementations, instead of directing light towards the retina 352 at slightly different angles using all the multiple light sources 310, respectively, a better image of the retina 352 may result using the subset of the multiple light sources 310.

In some implementations, selectively enabling a subset of the light sources 310 based on gaze direction may conserve power, reduce glare, or reduce the number of ineffective illumination sources.

In some implementations, selective illumination (e.g., less illumination) using the subset of the multiple light sources 310 reduces the glare at the image sensor 340 caused by light (e.g., intended to be illuminating the retina 352) reflecting on a cornea 354 back to saturate portions of the image sensor 340. In some implementations, the light reflecting off the cornea 354 may obscure or occlude the retina 352, which may interfere with gaze tracking.

In some implementations, glare 360 of reflected light off the cornea 354 is reduced or prevented by selectively turning on/off different ones of the multiple light sources 310 when choosing the subset of light sources in order to obtain a retinal image that is not impacted by corneal reflections. In a similar fashion, glare of reflected light off a crystalline lens 356 of the eye 350 is reduced or prevented by selectively turning on/off different ones of the multiple light sources 310 when choosing the subset of light sources in order to obtain a retinal image that is not impacted by reflections off the crystalline lens 356.

Figure 4:
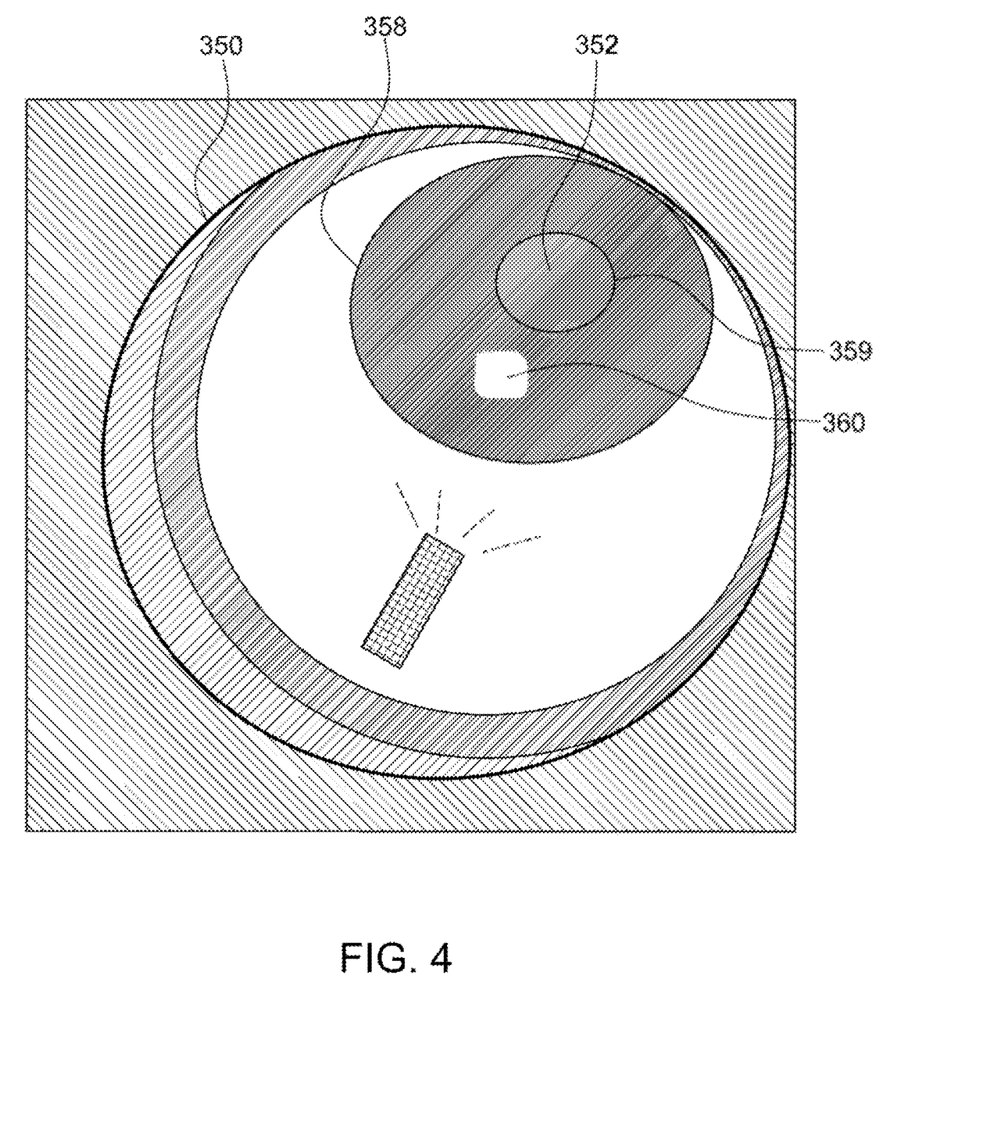
FIG. 4 is a diagram that illustrates glare from exemplary light sources used to illuminate a retina in accordance with some implementations.

FIG. 4 is a diagram that illustrates glare from exemplary light sources used to illuminate a retina in accordance with some implementations. As shown in FIG. 4, glare 360 of reflected light off the cornea 354 may saturate portions of an image of the eye 350 produced by the image sensor 340. When the saturation of the image sensor 340 caused by the glare 360 aligns with the retina 352, the image of the retina 352 may be obstructed. As shown in FIG. 4, significant glare 360 occurs when illuminating portions of the retina 352 through an iris 359 of a pupil 358 of the eye 350. In addition, a size of the pupil 358 varies among people, and the glare 360 may cause increased occlusion of the retina 352 with smaller pupils (e.g., the occlusion may be large enough to cover the entire pupil or iris).

In some implementations, one or more of the multiple light sources 310 will illuminate portions of the retina 352 that have very few or no features (e.g., blood vessels). During retinal imaging-based gaze tracking, analyzing featureless portions of the retina 352 increases computations needed for retinal image processing without benefit (e.g., without improving gaze tracking). In some implementations, when trying to determine the orientation of the eye 350 from a current retinal image, featureless portions of the retina 352 may be identified and ignored, and corresponding ones of the multiple light sources 310 not selected for the subset of light sources (e.g., disabled). In some implementations disabling ones of the subset of the multiple light sources 310 that illuminate featureless portions of the retina 352 based on gaze direction reduces energy consumption during retinal imaging-based gaze tracking.

Example operations of retinal imaging-based gaze tracking will now be described. In some implementations, a first phase of retinal imaging-based gaze tracking is "enrollment". In some implementations, a second phase of retinal imaging-based gaze tracking is "gaze detection" or active gaze tracking.

In some implementations, enrollment is used to generate a map of the retina 352 based on gaze direction (e.g., eye orientation). Thus, while wearing an electronic device such as an HMD, a user is instructed to look in several different specific locations (e.g., left to right and top to bottom) and an image of the retina while looking at each specific location is generated. In some implementations, while looking at each of the specific locations, any of the multiple light sources 310 that cause glare (e.g., the glare 360) are identified (e.g., for potential exclusion). In some implementations, while looking at each of the specific locations, any of the multiple light sources 310 that illuminate featureless portions of the retina are identified (e.g., for potential exclusion). Then, in some implementations, the individual images (e.g., maps of portions of the retina) for each of the specific locations are combined into sectional maps of the retina 352 or a single, larger, combined map of the retina 352. During subsequent retinal imaging-based active gaze tracking, matching a current view of a portion of the retina 352 to the enrollment map of the retina (e.g., individual maps, sectional maps, or the combined retina map), identifies or determines a current gaze direction of the eye 350.

Initially, during retinal image based active gaze tracking, all or a predetermined sequence of the multiple light sources 310 are enabled and the image sensor 340 takes a current image of the retina 352. Once the current image of the retina 352 is identified in the combined retina map, an eye orientation or a current gaze direction of the eye 350 is known and a number of light sources 310 being used can be reduced (e.g., the subset of light sources 310 identified for that gaze direction may be used).

In some implementations, the reduced number of light sources in the subset of light sources 310 may be used until there is a large movement of the eye 350 (e.g., over a threshold amount). Alternatively, in some implementations, the subset of light sources 310 may be used until a resulting current image of the retina 352 does not match the map of the retina for that gaze direction. In some implementations, when the current gaze direction changes, the image sensor 340 takes images of the retina 352 while all of the multiple light sources 310 are enabled until the current retinal image is again matched to the enrollment retina map, and the subset of light sources 310 for that gaze direction are used. In some implementations, the subset of light sources excludes/disables unused lights, lights that cause glare, lights that illuminate featureless regions, or lights that are redundant (e.g., within the multiple light sources 310) to reduce the number of lights in the subset of light sources 310 used for a specific gaze.

Figure 5:
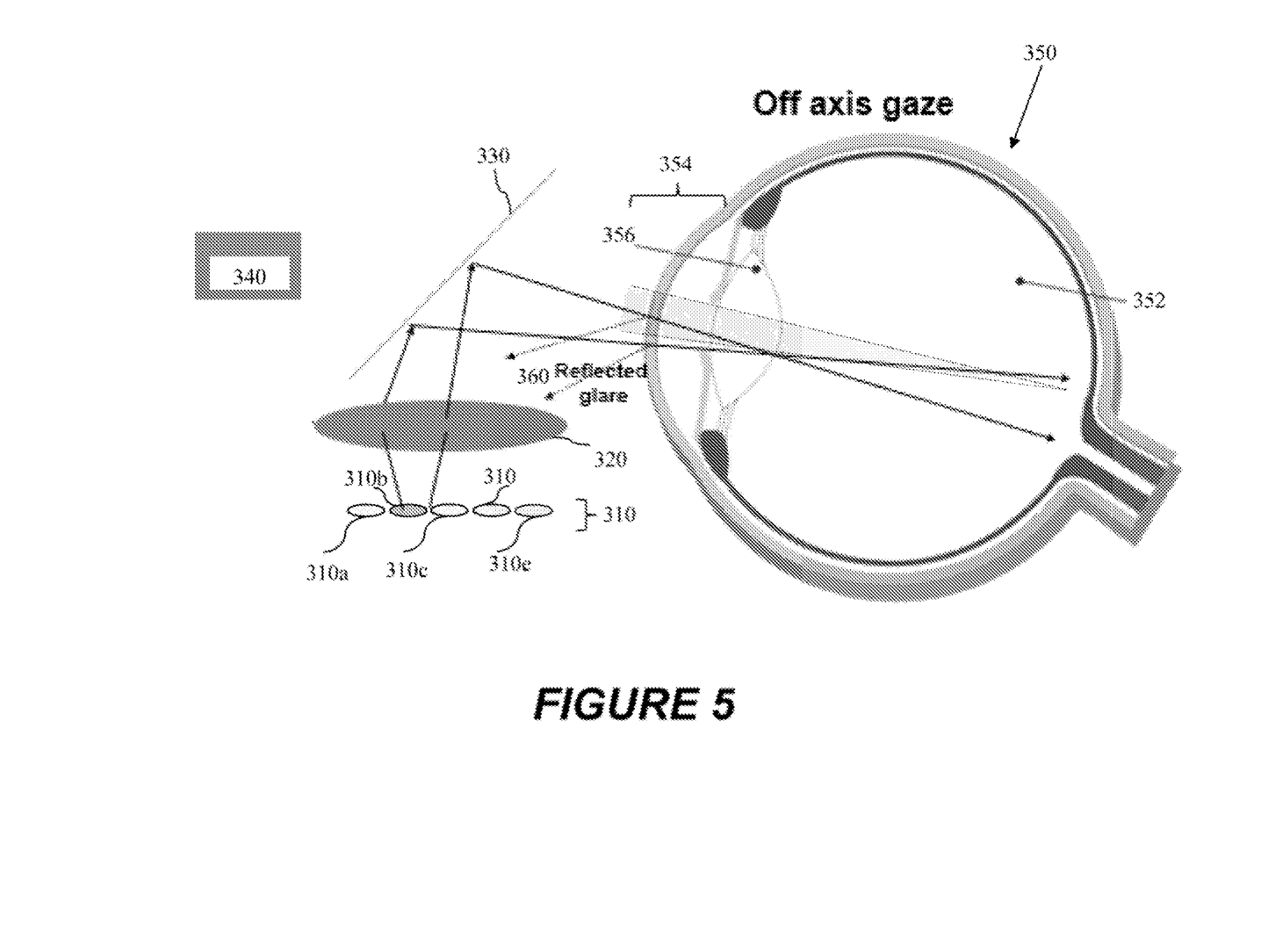
FIG. 5 is a block diagram that illustrates an exemplary tracking system that selectively uses a subset of multiple light sources to illuminate one or more portions of a retina for gaze tracking in accordance with some implementations.

FIG. 5 is a block diagram that illustrates an exemplary eye tracking system that selectively uses a subset of multiple light sources to illuminate one or more portions of a retina for gaze tracking in accordance with some implementations. As shown in FIG. 5, the only enabled light source 310c of the light sources 310 uses the beam splitter 330 to provide off-axis illumination. Some implementations combine on-axis and off-axis illumination-based eye assessments.

In some implementations, the multiple light sources 310 may use a single collimation lens 320 or a collimating lens for each of the individual light sources 310a, 310b, ..., 310e. In some implementations, the multiple light sources 310 are directional light sources. In some implementations, the multiple light sources 310 are a 1D array of light sources. In some implementations, the multiple light sources 310 are a 2D array of light sources (e.g., a ring or rectangle around the image sensor). In some implementations, the multiple light sources 310 are a 3D array of light sources (e.g., not arranged in a single plane). In some implementations, the light sources 310 include several hundred or several thousand VCSELs.

Figure 6:
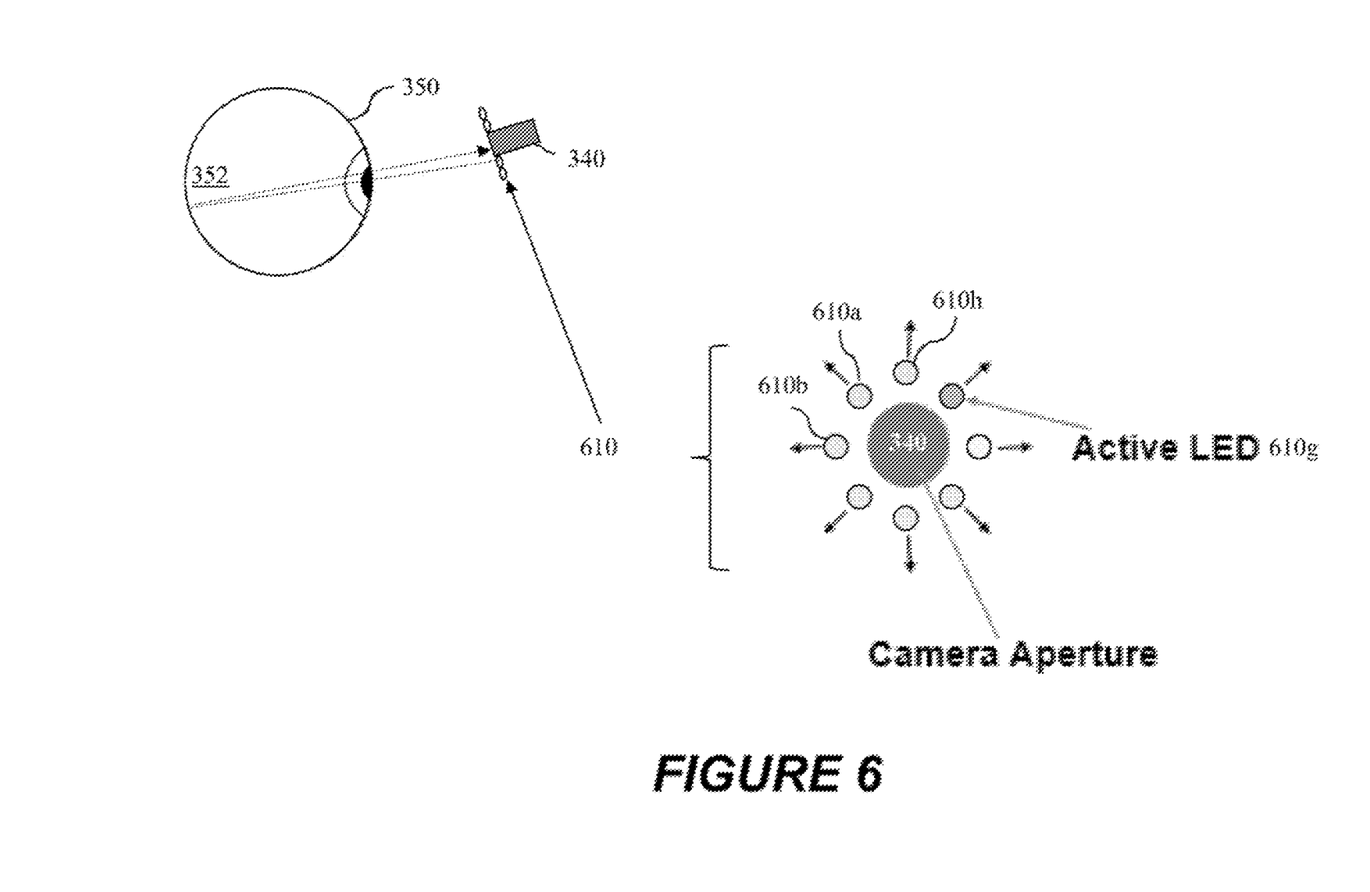
FIG. 6 is a diagram that illustrates exemplary light sources near an image sensor used to illuminate a retina in accordance with some implementations.

FIG. 6 is a diagram that illustrates exemplary light sources near an image sensor used to illuminate a retina in accordance with some implementations. As shown in FIG. 6, the multiple lights sources 610 produce light that illuminates different portions of the retina 352 to be captured by the image sensor 340 (e.g., IR camera). In some implementations, a subset of multiple light sources 610 illuminate one or more portions of the retina 352 for gaze tracking. In some implementations, the multiple lights sources 610 are directional light sources (e.g., LEDs). As shown in FIG. 6, the only enabled light source 610g of the light sources 310 is near the optics of the image sensor 340 and provides approximately on-axis retinal illumination according to some implementations.

Figure 7:
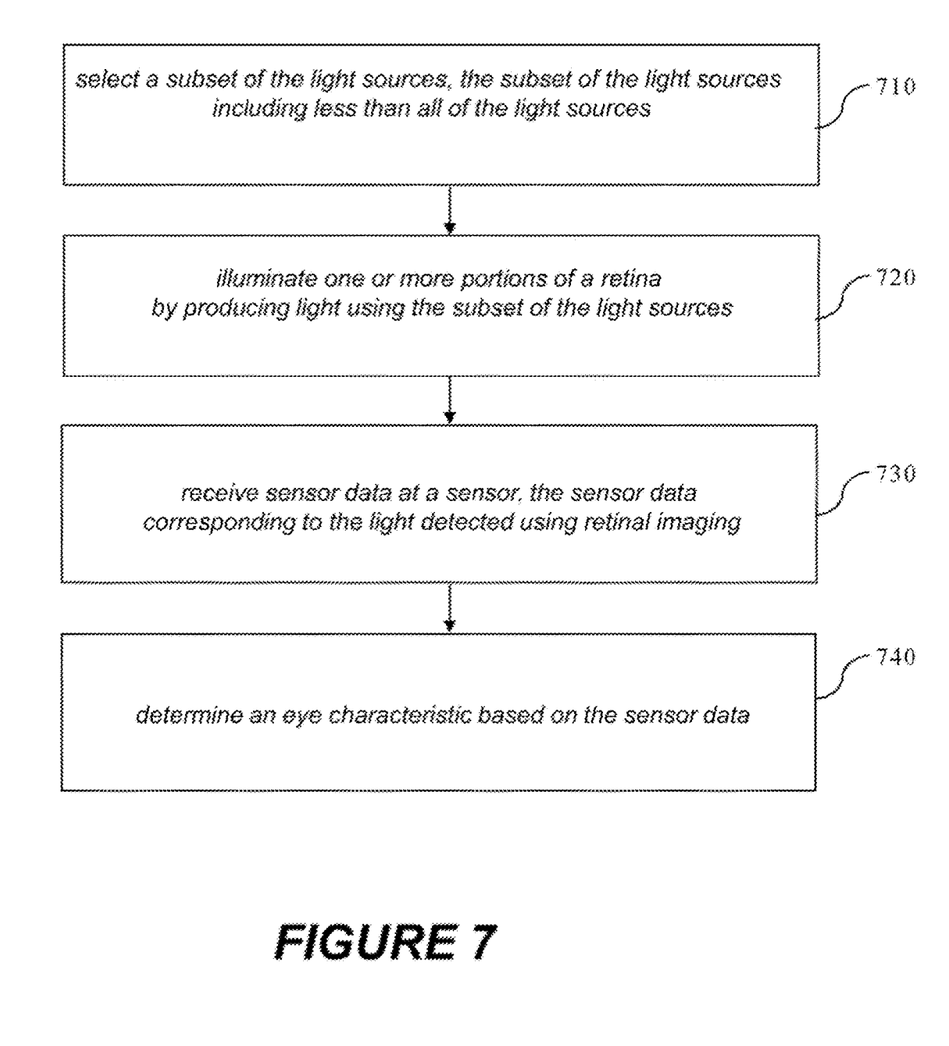
FIG. 7 is a flowchart illustrating an exemplary method of tracking a user's gaze based on a retinal imaging technique that selectively uses a subset of light sources to illuminate one or more portions of the retina in accordance with some implementations.

FIG. 7 is a flowchart illustrating an exemplary method of tracking a user's gaze based on a retinal imaging technique that selectively uses a subset of light sources to illuminate one or more portions of the retina in accordance with some implementations. In some implementations, the subset of the light sources is less than all the light sources and provides better gaze tracking using retinal imaging by reducing glare, reducing image saturation, reducing imaging computation, or reducing energy consumption. In some implementations, the method 700 is performed by a device (e.g., electronic device 120, 200 of FIGS. 1-2). The method 700 can be performed using an electronic device or by multiple devices in communication with one another. In some implementations, the method 700 is performed by processing logic, including hardware, firmware, software, or a combination thereof. In some implementations, the method 700 is performed by a processor executing code stored in a non-transitory computer-readable medium (e.g., a memory). In some implementations, the method 700 is performed by an electronic device having a processor and light sources.

At block 710, the method 700 selects a subset of the light sources, the subset of the light sources including less than all of the light sources. In some implementations, the light sources are a 1D, 2D or 3D array of light sources. In some implementations, the light sources are one or more rings or polygons of light sources. In some implementations, the light sources are LEDs or VCSELs. In some implementations, the light sources are individually addressable (e.g., enabled or disabled).

At block 720, the method 700 illuminates one or more portions of a retina by producing light using the subset of the light sources (e.g., retinal imaging). In some implementations, the light sources illuminate different locations on the retina. In some implementations, the light sources may provide lights at different angles to illuminate different locations on the retina. In some implementations, the light sources may provide directional lights to illuminate different locations on the retina. In some implementations, the light sources use a single collimation lens. In some implementations, the light sources use a separate collimating lens for every individual light source. In some implementations, the subset of the light sources illuminate a small portion of the retina.

At block 730, the method 700 receives sensor data at a sensor, the sensor data corresponding to the light detected or obtained during retinal imaging. In some implementations, an image sensor receives image sensor data that corresponds to the light reflected or scattered from the retina. In some implementations, an IR camera receives IR image data corresponding to the light reflected from the retina. In some implementations, the sensor receives an IR image of the retina corresponding to the light reflected from the retina. In some implementations, the sensor is part of a scanning apparatus or the sensor data is obtained using a scanning apparatus. For example, the received image may be formed using a point-by-point scanning apparatus or a line-by-line scanning apparatus. In some implementations, retinal imaging is performed using a scanning mirror and a single photodetector. For example, the scanning mirror and the single photodetector may be in a confocal arrangement.

At block 740, the method 700 determines an eye characteristic based on the sensor data. In some implementations, the eye characteristic includes an eye gaze direction, an eye orientation, etc. based on the sensor data. In some implementations, the eye characteristic is determined by comparing an image of the retina (the sensor data) to a previously-generated map of the retina. In some implementations, the previously-generated map of the retina may be generated during an enrollment process.

In some implementations, the subset of the light sources is selected based on a previously-detected eye characteristic (e.g., based on an initial/prior gaze direction or eye orientation). In some implementations, the previously-detected eye characteristic is determined using light produced using more than the subset of light sources (e.g., at least one more light source than the subset of light sources) and a map of the retina. For example, all of the light sources may be turned on to illuminate the entire retinal field when a HMD user turns on gaze tracking at the HMD.

In some implementations, the method at block 740 continues to receive the sensor data and determine the eye characteristic until an eye change event is detected. In some implementations, the eye change event is a change in eye orientation or gaze direction that exceeds a threshold. In some implementations, upon detecting the eye change event, the eye characteristic is re-determined using light produced by more than the subset of light sources (e.g., most of the light sources, all of the light sources, or at least one more light source than the subset of light sources) and a map of the retina.

In some implementations, one or more additional criterion may be used to select the subset of light sources. In some implementations, the subset of light sources is selected by determining that a first light source of the light sources is producing an imaging defect (e.g., glare, saturation, etc.) in retinal images obtained via the sensor, and excluding the first light source from the subset of light sources. In some implementations, the subset of light sources is selected by selecting a second light source of the light sources based on the retinal pattern (e.g., sparseness of features like blood vessels, minimal number of features, or featureless) illuminated by the second light source, and excluding the second light source from the subset of light sources. In some implementations, the one or more additional criterion are based on the eye characteristic like gaze direction. In some implementations, the one or more additional criterion are determined during enrollment.

In some implementations, finding the gaze direction of the eye initially or the eye change event uses more/most/all of the light sources. In some implementations, more/most/all of the light sources are used to illuminate a larger portion of the retina. Then, once the gaze direction is determined, a reduced set of the light sources is selected (e.g., the subset of light sources) and used to track or monitor small eye movements until the eye change event occurs again.

In some implementations, the method 700 further includes retinal imaging-based gaze tracking using both eyes of user. In some implementations, the sensor data may be a still image, series of images, video, etc., which may include depth information such as a corresponding depth map.

Figure 8:
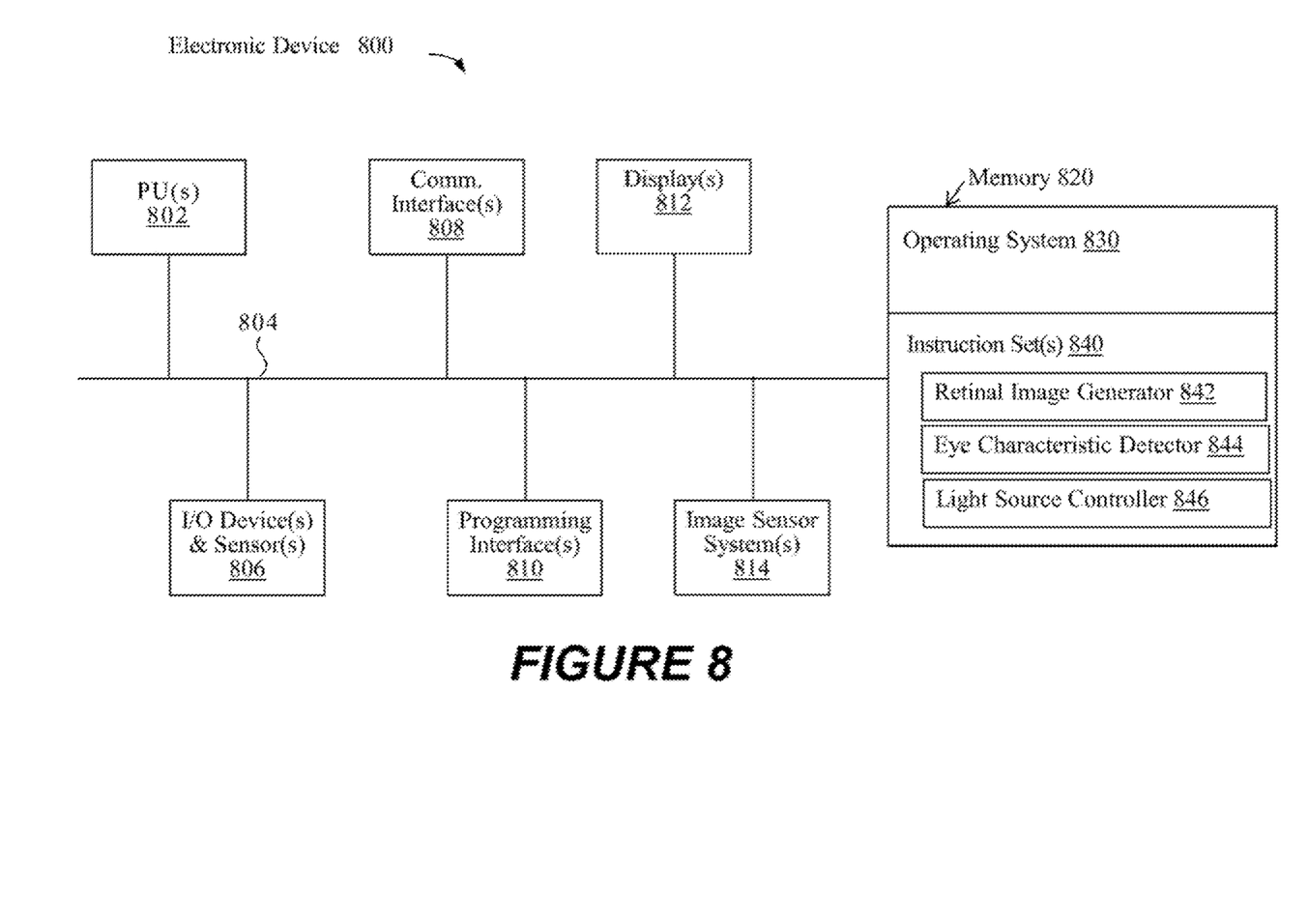
FIG. 8 illustrates an example electronic device in accordance with some implementations.

FIG. 8 is a block diagram of an example device 800. Device 800 illustrates an exemplary device configuration for the device 120. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, in some implementations the electronic device 800 includes one or more processing units 802 (e.g., microprocessors, ASICs, FPGAs, GPUs, CPUs, processing cores, or the like), one or more input/output (I/O) devices and sensors 806, one or more communication interfaces 808 (e.g., USB, FIREWIRE, THUNDERBOLT, IEEE 802.3x, IEEE 802.11x, IEEE 802.16x, GSM, CDMA, TDMA, GPS, IR, BLUETOOTH, ZIGBEE, SPI, I2C, or the like type interface), one or more programming (e.g., I/O) interfaces 810, one or more displays 812, one or more interior or exterior facing sensor systems 814, a memory 820, and one or more communication buses 804 for interconnecting these and various other components.

In some implementations, the one or more communication buses 804 include circuitry that interconnects and controls communications between system components. In some implementations, the one or more I/O devices and sensors 806 include at least one of an inertial measurement unit (IMU), an accelerometer, a magnetometer, a gyroscope, a thermometer, one or more physiological sensors (e.g., blood pressure monitor, heart rate monitor, blood oxygen sensor, blood glucose sensor, etc.), one or more microphones, one or more speakers, a haptics engine, one or more depth sensors (e.g., a structured light, a time-of-flight, or the like), or the like.

In some implementations, the one or more displays 812 are configured to present content to the user. In some implementations, the one or more displays 812 correspond to holographic, digital light processing (DLP), liquid-crystal display (LCD), liquid-crystal on silicon (LCoS), organic light-emitting field-effect transitory (OLET), organic light-emitting diode (OLED), surface-conduction electron-emitter display (SED), field-emission display (FED), quantum-dot light-emitting diode (QD-LED), micro-electromechanical system (MEMS), or the like display types. In some implementations, the one or more displays 812 correspond to diffractive, reflective, polarized, holographic, etc. waveguide displays. For example, the electronic device 800 may include a single display. In another example, the electronic device 800 includes a display for each eye of the user.

In some implementations, the one or more interior or exterior facing sensor systems 814 include an image capture device or array that captures image data or an audio capture device or array (e.g., microphone) that captures audio data. The one or more image sensor systems 814 may include one or more RGB cameras (e.g., with a complimentary metal-oxide-semiconductor (CMOS) image sensor or a charge-coupled device (CCD) image sensor), monochrome cameras, IR cameras, event-based cameras, or the like. In various implementations, the one or more image sensor systems 814 further include an illumination source that emits light such as a flash. In some implementations, the one or more image sensor systems 814 further include an on-camera image signal processor (ISP) configured to execute a plurality of processing operations on the image data.

The memory 820 includes high-speed random-access memory, such as DRAM, SRAM, DDR RAM, or other random-access solid-state memory devices. In some implementations, the memory 820 includes non-volatile memory, such as one or more magnetic disk storage devices, optical disk storage devices, flash memory devices, or other non-volatile solid-state storage devices. The memory 820 optionally includes one or more storage devices remotely located from the one or more processing units 802. The memory 820 comprises a non-transitory computer readable storage medium.

In some implementations, the memory 820 or the non-transitory computer readable storage medium of the memory 820 stores an optional operating system 830 and one or more instruction set(s) 840. The operating system 830 includes procedures for handling various basic system services and for performing hardware dependent tasks. In some implementations, the instruction set(s) 840 include executable software defined by binary information stored in the form of electrical charge. In some implementations, the instruction set(s) 840 are software that is executable by the one or more processing units 802 to carry out one or more of the techniques described herein.

In some implementations, the instruction set(s) 840 include a retinal image generator 842 that is executable by the processing unit(s) 802 to capture sensor data representing a retina of a user of the device 800 according to one or more of the techniques disclosed herein.

In some implementations, the instruction set(s) 840 include an eye characteristic detector 844 that is executable by the processing unit(s) 802 to determine a gaze direction of the like of the user of the electronic device according to one or more of the techniques disclosed herein. In some implementations, the eye characteristic detector 844 is executed to compare a current retinal image with a map of the retina of the user of the electronic device.

In some implementations, the instruction set(s) 840 include a light source controller 846 that is executable by the processing unit(s) 802 to determine a subset of retinal imaging light sources to enable based on the gaze direction of the user of the electronic device according to one or more of the techniques disclosed herein. In some implementations, the subset of retinal imaging light sources is one or more and less than all of retinal imaging light sources.

Although the instruction set(s) 840 are shown as residing on a single device, it should be understood that in other implementations, any combination of the elements may be located in separate computing devices. FIG. 8 is intended more as a functional description of the various features which are present in a particular implementation as opposed to a structural schematic of the implementations described herein. As recognized by those of ordinary skill in the art, items shown separately could be combined and some items could be separated. For example, actual number of instruction sets and the division of particular functions and how features are allocated among them will vary from one implementation to another and, in some implementations, depends in part on the particular combination of hardware, software, or firmware chosen for a particular implementation.

In some implementations, the electronic device 800 is a head mounted system including one or more speaker(s) and an integrated opaque display. Alternatively, the head mounted system may be configured to accept an external opaque display (e.g., a smartphone). Rather than an opaque display, the head mounted system may have a transparent or translucent display. The transparent or translucent display may have a medium through which light representative of images is directed to a person's eyes. The display may utilize digital light projection, OLEDs, LEDs, uLEDs, liquid crystal on silicon, laser scanning light source, or any combination of these technologies. The medium may be an optical waveguide, a hologram medium, an optical combiner, an optical reflector, or any combination thereof. In one embodiment, the transparent or translucent display may be configured to become opaque selectively. Projection-based systems may employ retinal projection technology that projects graphical images onto a person's retina. Projection systems also may be configured to project virtual objects into the physical environment, for example, as a hologram or on a physical surface.

It will be appreciated that the implementations described above are cited by way of example, and that the present invention is not limited to what has been particularly shown and described hereinabove. Rather, the scope includes both combinations and sub combinations of the various features described hereinabove, as well as variations and modifications thereof which would occur to persons skilled in the art upon reading the foregoing description and which are not disclosed in the prior art.

As described above, one aspect of the present technology is the gathering and use of physiological data to improve a user's experience of an electronic device. The present disclosure contemplates that in some instances, this gathered data may include personal information data that uniquely identifies a specific person or can be used to identify interests, traits, or tendencies of a specific person. Such personal information data can include physiological data, demographic data, location-based data, telephone numbers, email addresses, home addresses, device characteristics of personal devices, or any other personal information.

The present disclosure recognizes that the use of such personal information data, in the present technology, can be used to the benefit of users. For example, the personal information data can be used to improve the content viewing experience. Accordingly, use of such personal information data may enable calculated control of the electronic device. Further, other uses for personal information data that benefit the user are also contemplated by the present disclosure.

The present disclosure further contemplates that the entities responsible for the collection, analysis, disclosure, transfer, storage, or other use of such personal information and/or physiological data will comply with well-established privacy policies and/or privacy practices. In particular, such entities should implement and consistently use privacy policies and practices that are generally recognized as meeting or exceeding industry or governmental requirements for maintaining personal information data private and secure. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates implementations in which users selectively block the use of, or access to, personal information data. That is, the present disclosure contemplates that hardware or software elements can be provided to prevent or block access to such personal information data. For example, in the case of user-tailored content delivery services, the present technology can be configured to allow users to select to "opt in" or "opt out" of participation in the collection of personal information data during registration for services. In another example, users can select not to provide personal information data for targeted content delivery services. In yet another example, users can select to not provide personal information, but permit the transfer of anonymous information for the purpose of improving the functioning of the device.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences or settings based on non-personal information data or a bare minimum amount of personal information, such as the content being requested by the device associated with a user, other non-personal information available to the content delivery services, or publicly available information.

In some embodiments, data is stored using a public/private key system that only allows the owner of the data to decrypt the stored data. In some other implementations, the data may be stored anonymously (e.g., without identifying and/or personal information about the user, such as a legal name, username, time and location data, or the like). In this way, other users, hackers, or third parties cannot determine the identity of the user associated with the stored data. In some implementations, a user may access their stored data from a user device that is different than the one used to upload the stored data. In these instances, the user may be required to provide login credentials to access their stored data.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Unless specifically stated otherwise, it is appreciated that throughout this specification discussions utilizing the terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general purpose computing apparatus to a specialized computing apparatus implementing one or more implementations of the present subject matter. Any suitable programming, scripting, or other type of language or combinations of languages may be used to implement the teachings contained herein in software to be used in programming or configuring a computing device.

Implementations of the methods disclosed herein may be performed in the operation of such computing devices. The order of the blocks presented in the examples above can be varied for example, blocks can be re-ordered, combined, or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or value beyond those recited. Headings, lists, and numbering included herein are for ease of explanation only and are not meant to be limiting.

It will also be understood that, although the terms "first," "second," etc. may be used herein to describe various objects, these objects should not be limited by these terms. These terms are only used to distinguish one object from another. For example, a first node could be termed a second node, and, similarly, a second node could be termed a first node, which changing the meaning of the description, so long as all occurrences of the "first node" are renamed consistently and all occurrences of the "second node" are renamed consistently. The first node and the second node are both nodes, but they are not the same node.

The terminology used herein is for the purpose of describing particular implementations only and is not intended to be limiting of the claims. As used in the description of the implementations and the appended claims, the singular forms "a," "an," and "the" are intended to include the plural forms as well, unless the context clearly indicates otherwise. It will also be understood that the term "or" as used herein refers to and encompasses any and all possible combinations of one or more of the associated listed items. It will be further understood that the terms "comprises" or "comprising," when used in this specification, specify the presence of stated features, integers, steps, operations, objects, or components, but do not preclude the presence or addition of one or more other features, integers, steps, operations, objects, components, or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The foregoing description and summary of the invention are to be understood as being in every respect illustrative and exemplary, but not restrictive, and the scope of the invention disclosed herein is not to be determined only from the detailed description of illustrative implementations, but according to the full breadth permitted by patent laws. It is to be understood that the implementations shown and described herein are only illustrative of the principles of the present invention and that various modification may be implemented by those skilled in the art without departing from the scope and spirit of the invention.

What is claimed is:

1. A method comprising:
at an electronic device having a processor and a plurality of light sources configured to direct light at a retina:
selecting a subset of the light sources, the subset of the light sources comprising less than all of the light sources, wherein each of the light sources directs light towards a respective region on the retina, at least some of the regions at least partially different from one another;
illuminating the subset of the light sources to direct light toward one or more portions of the retina;
receiving sensor data at a sensor, the sensor data corresponding to the light reflected from the retina; and
determining an eye characteristic based on the sensor data.

2. The method of claim 1, wherein the eye characteristic is a gaze direction or eye orientation.

3. The method of claim 1, wherein the subset of the light sources is selected based on a previously-detected eye characteristic.

4. The method of claim 3, wherein the previously-detected eye characteristic is determined using light produced using more than the subset of light sources and a map of the retina.

5. The method of claim 1 further comprising continuing to receive the sensor data and determine the eye characteristic until an eye change event is detected, the eye change event corresponding to a change in eye orientation or gaze direction that exceeds a threshold.

6. The method of claim 5 further comprising, upon detecting the eye change event, redetermining the eye characteristic using light produced using more than the subset of light sources and a map of the retina.

7. The method of claim 1, wherein the subset of lights sources is selected by:
determining that a first light source of the light sources is producing an imaging defect in retinal images obtained via the sensor; and
in accordance with determining that the light source is producing the imaging defect, excluding the first light source from the subset of light sources.

8. The method of claim 7, wherein the imaging defect comprises glare or saturation.

9. The method of claim 1, wherein the subset of lights sources is selected by:
selecting a first light source of the light sources based on the retinal pattern illuminated by the first light source; and
excluding the first light source from the subset of light sources.

10. The method of claim 1, wherein the light is infrared (IR) light.

11. A device comprising:
light sources configured to direct light at a retina;
a sensor configured provide sensor data;
a processor; and
a computer-readable storage medium comprising instructions that upon execution by the processor cause the system to perform operations, the operations comprising:
selecting a subset of the light sources, the subset of the light sources comprising less than all of the light sources, wherein each of the light sources directs light towards a respective region on the retina, at least some of the regions at least partially different from one another;
illuminating the subset of the light sources to direct light toward one or more portions of the retina;
receiving the sensor data at the sensor, the sensor data corresponding to the light reflected from the retina; and
determining an eye characteristic based on the sensor data.

12. The device of claim 11, further comprising a single collimator through which light from all of the light sources is directed.

13. The device of claim 11, wherein each light source of the light sources uses a separate collimator.

14. The device of claim 11, wherein each light source of the light sources is a vertical-cavity surface-emitting laser (VCSEL).

15. The device of claim 11, wherein at least one of the light sources is aligned approximately on axis with an optical axis of the sensor.

16. The device of claim 15, wherein approximately on-axis illumination is produced via a light source sufficiently near optics of the sensor such that the light source produces a light ray that provides a reflection off the retina that is captured by the optics of sensor.

17. The device of claim 16, wherein the approximately on-axis illumination is produced via a light source ring around optics of the sensor.

18. The device of claim 11, wherein the electronic device is a head-mounted device (HMD).

19. A non-transitory computer-readable storage medium, storing program instructions computer-executable on a computer to perform operations comprising:
selecting a subset of light sources configured to direct light at a retina, the subset of light sources comprising less than all of the light sources, wherein each of the light sources directs light towards a respective region on the retina, at least some of the regions at least partially different from one another;
illuminating the subset of the light sources to direct light toward one or more portions of the retina;
receiving sensor data at a sensor, the sensor data corresponding to the light reflected from the retina; and
determining an eye characteristic based on the sensor data.

* * * * *

UNITED STATES PATENT AND TRADEMARK OFFICE
CERTIFICATE OF CORRECTION

| | |
|---|---|
| PATENT NO. | : 12,073,018 B2 |
| APPLICATION NO. | : 18/026881 |
| DATED | : August 27, 2024 |
| INVENTOR(S) | : Eran Tal and Ariel Lipson |

It is certified that error appears in the above-identified patent and that said Letters Patent is hereby corrected as shown below:

In the Claims

Claim 11, Column 16, Line 3, reads:
"… a sensor configured provide sensor data; …"
Should read:
--… a sensor configured to provide sensor data; …--

Signed and Sealed this
First Day of October, 2024

Katherine Kelly Vidal
*Director of the United States Patent and Trademark Office*